United States Patent
Wegener et al.

(10) Patent No.: US 12,296,086 B2
(45) Date of Patent: May 13, 2025

(54) SYSTEMS AND METHODS FOR PROCESSING LARGE VOLUMES OF BIOLOGICAL FLUID

(71) Applicant: Fenwal, Inc., Lake Zurich, IL (US)

(72) Inventors: Christopher J. Wegener, Libertyville, IL (US); Steven C. Binninger, Evanston, IL (US); Alaina Schlinker, Chicago, IL (US); Bret Olson, Evanston, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 16/143,849

(22) Filed: Sep. 27, 2018

(65) Prior Publication Data

US 2019/0099545 A1    Apr. 4, 2019

Related U.S. Application Data

(60) Provisional application No. 62/565,949, filed on Sep. 29, 2017.

(51) Int. Cl.
*A61M 1/36* (2006.01)
*A61M 1/02* (2006.01)
(Continued)

(52) U.S. Cl.
CPC ........ *A61M 1/3692* (2014.02); *A61M 1/0209* (2013.01); *A61M 1/0272* (2013.01);
(Continued)

(58) Field of Classification Search
CPC .............. A61M 1/3692; A61M 1/0209; A61M 1/0272; A61M 1/0281; A61M 1/3693; A61M 2205/3379; A61M 1/265; A61M 1/34; A61M 1/0236; A61M 1/3403; A61M 1/3496; A61M 1/3696; A61M 1/0218; A61M 1/262; A61M 1/38; A61M 2205/3331; A61M 2205/3393; A61M 2205/50; A61M 1/00; A61M 1/0231; A61M 1/025; A61M 1/3472; A61M 1/36; A61M 1/3601; A61M 1/3603; A61M 1/3644; A61M 1/3672; A61M 2202/0429;
(Continued)

(56) References Cited

U.S. PATENT DOCUMENTS 3,486,145 A   12/1969 Paige
5,053,121 A   10/1991 Schoendorfer et al.
(Continued)

FOREIGN PATENT DOCUMENTS

EP   1128887 A1   9/2001
WO   0117652 A1   3/2001
(Continued)

OTHER PUBLICATIONS

European Search Report and Opinion Issued by the European Patent Office for Application No. 18196856.8, dated Feb. 12, 2019 (8 pages total).

*Primary Examiner* — Fred Prince
(74) *Attorney, Agent, or Firm* — Cook Alex Ltd.

(57) ABSTRACT

Automated systems and methods for processing a biological cell suspension are disclosed. The systems and methods allow for the processing of large volumes of a biological cell suspension contained in or more source containers.

18 Claims, 7 Drawing Sheets

(51) Int. Cl.
*C12N 5/078* (2010.01)
*C12M 1/00* (2006.01)

(52) U.S. Cl.
CPC ......... *A61M 1/0281* (2013.01); *C12N 5/0634* (2013.01); *A61M 1/3693* (2013.01); *A61M 2205/3379* (2013.01); *C12M 47/04* (2013.01); *C12N 2509/00* (2013.01)

(58) Field of Classification Search
CPC .... A61M 2202/0439; A61M 2205/502; A61M 2205/75; A61M 1/341; A61M 1/342; A61M 1/3633; A61M 1/3635; A61M 1/3643; A61M 1/3649; A61M 1/365; A61M 1/3687; A61M 2205/3334; A61M 2205/60; A61M 2205/6072; A61M 2205/7554; B01D 2311/04; B01D 2315/02; B01D 63/16; B01D 2311/2619; B01D 2311/2676; B01D 61/00; B01D 61/18; B01D 63/062; B01D 19/0068; B01D 21/262; B01D 2221/10; B01D 2313/48; B01D 2313/90; B01D 2321/02; B01D 61/025; B01D 61/145; B01D 61/16; B01D 61/22; B01D 63/065; B01D 65/02; B01D 71/40; B01D 71/50; B01D 2313/08; B01D 2313/20; B01D 2313/243; B01D 2321/2091; B01D 61/246; B01D 63/06; B01D 65/08; B04B 5/0442; B04B 11/04; B04B 13/00; B04B 2005/045; B04B 2005/0464; A61K 35/16; A61K 9/0019; A61P 7/00; C12M 37/02; C12M 47/04; C12N 5/0641; C12N 5/0634; F04C 2270/041; G16H 10/40; Y10T 29/49826; A01N 1/0242

USPC ........................................ 210/645, 646, 647
See application file for complete search history.

(56) References Cited

U.S. PATENT DOCUMENTS

| | | | | |
|---|---|---|---|---|
| 5,194,145 | A * | 3/1993 | Schoendorfer | A61M 1/3496 210/321.63 |
| 6,251,295 | B1 * | 6/2001 | Johnson | A61M 1/3618 210/651 |
| 6,691,047 | B1 * | 2/2004 | Fredericks | A61M 1/3621 702/47 |
| 2002/0179544 | A1 * | 12/2002 | Johnson | A61M 1/3692 210/806 |
| 2003/0233064 | A1 | 12/2003 | Arm et al. | |
| 2013/0334139 | A1 * | 12/2013 | Blickhan | A61M 1/0281 210/650 |
| 2014/0039373 | A1 * | 2/2014 | Ragusa | A61M 1/3693 604/5.01 |
| 2015/0166957 | A1 * | 6/2015 | Kusters | A01N 1/0242 435/2 |
| 2016/0144098 | A1 * | 5/2016 | Radwanski | B01D 65/08 210/651 |
| 2016/0177262 | A1 * | 6/2016 | Wegener | B01D 63/062 435/2 |
| 2017/0274134 | A1 * | 9/2017 | Min | A61M 1/3692 |
| 2017/0340783 | A1 | 11/2017 | Wegener et al. | |
| 2017/0340799 | A1 | 11/2017 | Schlinker et al. | |
| 2018/0318348 | A1 * | 11/2018 | Corash | A61K 35/16 |

FOREIGN PATENT DOCUMENTS

| | | |
|---|---|---|
| WO | 2012125457 A1 | 9/2012 |
| WO | 2012125470 A1 | 9/2012 |
| WO | 2012154572 A1 | 11/2012 |

* cited by examiner

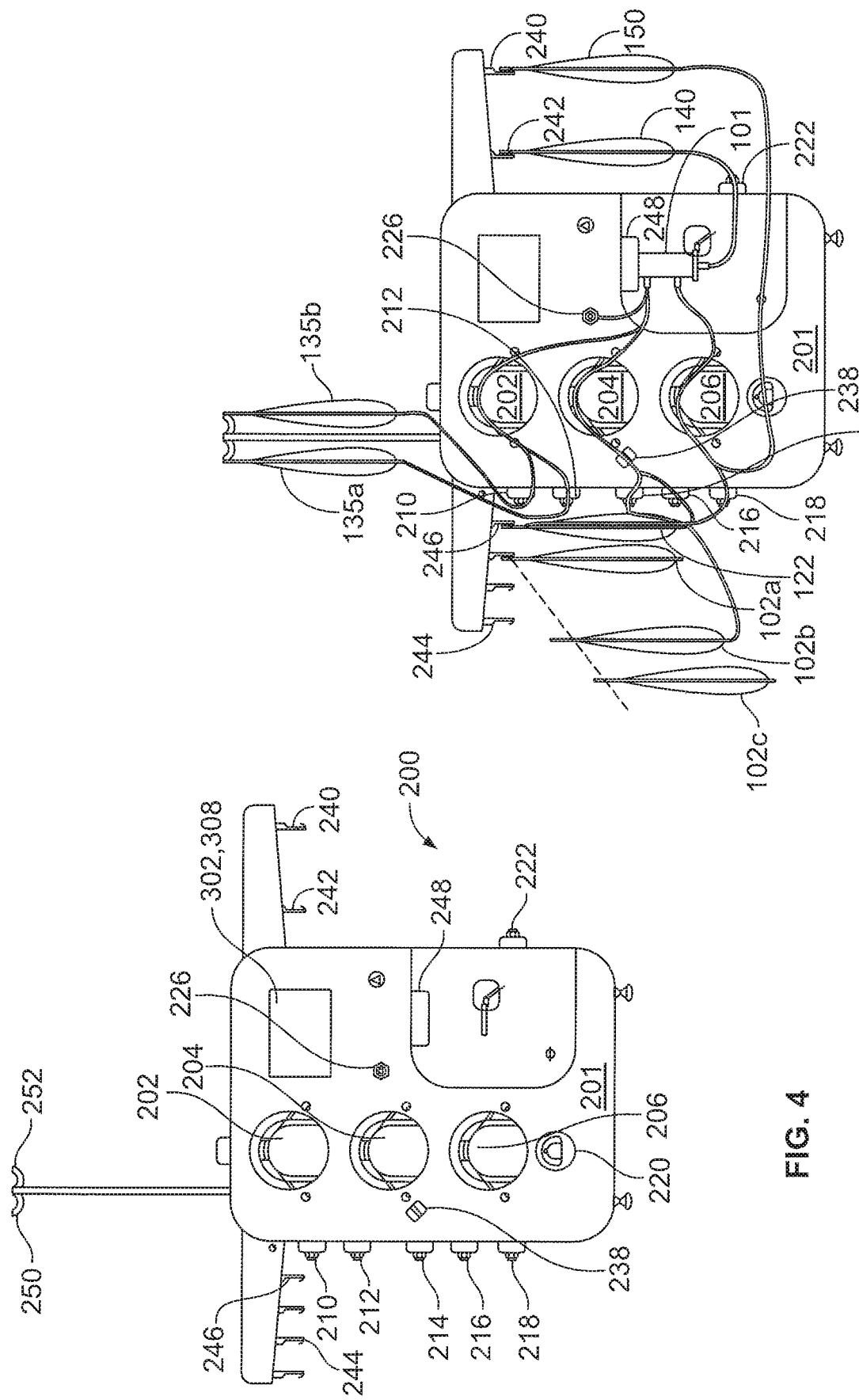

SYSTEMS AND METHODS FOR PROCESSING LARGE VOLUMES OF BIOLOGICAL FLUID

CROSS-REFERENCE TO RELATED APPLICATION

This application claims the benefit of and priority to U.S. Provisional Patent Application Ser. No. 62/565,949, filed on Sep. 29, 2017, the disclosure of which is incorporated herein by reference in its entirety.

FIELD OF THE DISCLOSURE

The present disclosure is directed to systems and methods for processing suspensions of biological fluid. More particularly, the present disclosure is directed to systems and methods for processing large volumes of biological cell suspensions using a single fluid circuit. Even more particularly, the present disclosure is directed to systems and methods for automatically controlling the processing of large volumes of biological cell suspensions from one or more containers of such suspensions.

BACKGROUND

Biological cells may be processed for a variety of reasons. For example, blood cells previously collected may be washed and/or concentrated for subsequent use as part of a therapy. The processing of biological fluids such as biological cells, blood or blood components typically involves using a reusable processing apparatus ("hardware") and a disposable fluid circuit adapted for mounting or other association with the hardware. The fluid circuit typically includes, among other things, a separation device, (plastic) containers and associated tubing that defines a flow path through the circuit.

The processing of biological cell suspensions for the purpose of arriving at a therapeutically useful concentration of cells often requires working with large volumes of source fluid and/or cryopreserved products. Large volumes of source fluid are often provided in multiple source containers or a single large-volume source container. In either case, the handling of large volumes presents challenges in managing the volume of the fluid to be processed within the confines of the disposable fluid circuit and/or the limits of the hardware and software capabilities. Often, in order to arrive at an effective concentration of cells, multiple procedures using multiple fluid circuits are carried out with the collected cells from each procedure being pooled together into a final product. This and other steps may also require additional human intervention or monitoring of the cell processing procedure(s) which may add time to the overall procedure. In the case of cryopreserved blood products, care must be exercised to ensure that previously frozen products do not thaw too quickly. Thus, the processing of multiple containers of cryopreserved products is typically performed one container at a time with separate disposable fluid circuits and separate entry of processing parameters required for each source container.

Accordingly, it would be desirable to have a more automated system that allows for one-time data entry for large volumes of biological cell suspensions to be processed, whether from multiple source containers or a single, larger-volume source container. It would be desirable to allow parameters such as starting concentrations of source fluid, target concentrations of the final product, total volumes of fluid to be processed and/or the number of source containers to be entered and received by the system at the beginning of the processing procedure, and have the automated system determine the manner in which source fluid is drawn from the source container(s). It would also be desirable to provide a system and method that requires a unitary fluid circuit that is adapted for use with such large volumes of source fluid, whether provided in one or multiple source containers.

SUMMARY

In one aspect, the present disclosure is directed to a system for processing biological cell suspensions. The system includes a disposable fluid circuit that includes a separation device, a fluid flow path in flow communication with the separation device, and one more fluid access devices for establishing fluid communication between the flow path and one or more source containers of a biological cell suspension. The system also includes a reusable hardware unit that houses a separation device drive unit for receiving the separation device, an operator input and a controller coupled to the input. The controller is configured (a) to receive a processing parameter such as the total volume of biological cell suspension to be processed from one or more source containers (b) to receive a processing parameter such as the concentration of cells in the one or more source containers and (c) to calculate the number of draws from the one or more source containers and the volume of each said draw.

In another aspect, the present disclosure is directed to an automated method for processing a biological cell suspension from one or more source containers of a biological cell suspension. The method includes at least the steps of (a) receiving a processing parameter such as the total volume of biological cell suspension to be processed from one or more source containers (b) receiving a processing parameter such as the concentration of cells in said one or more source containers (c) calculating the number of draws from the one or more source containers and the volume of each the draws and (d) drawing the biological cell suspension from the one or more source containers.

BRIEF DESCRIPTION OF THE DRAWINGS

FIG. 4 is a view of the front panel of the reusable processing apparatus;

FIG. 5 is another view of the front panel of a reusable processing apparatus with a disposable fluid circuit mounted thereon;

DETAILED DESCRIPTION OF THE EMBODIMENTS

The methods and systems disclosed herein typically employ a reusable separation apparatus and one or more disposable fluid circuits adapted for association with the reusable apparatus. The reusable separation apparatus may be any apparatus that can provide for the automated processing of biological cells, as well as automated preparation, such as priming, of the system prior to the processing of cells. By "automated," it is meant that the apparatus can be pre-programmed to carry out the system priming and cell processing steps without substantial operator involvement. Of course, even in the automated system of the present disclosure, it will be understood that some operator involvement will be required, including the loading or mounting of the disposable fluid circuit(s) onto the reusable apparatus, attachment of one or more source containers and entering certain processing parameters. Additional manual steps may be required as well. However, the reusable apparatus can be programmed to perform the processing of the biological cells through the disposable circuit(s) described below without substantial operator intervention.

Examples of a reusable apparatus include the Aurora® Plasmapheresis System and the Lovo Cell Processing System, both sold by Fenwal, Inc., a Fresenius Kabi Company, of Lake Zurich, Ill. Both the Aurora® Plasmapheresis System and the Lovo Cell Processing System are compact cell processors for washing and concentrating biological fluid such as certain blood cell components. The Lovo Cell Processing System uses a spinning membrane separator. A detailed description of a spinning membrane may be found in U.S. Pat. No. 5,194,145 to Schoendorfer, which is incorporated by reference herein in its entirety, and in International (PCT) Application No. PCT/US2012/028492, filed Mar. 9, 2012, the contents of which is also incorporated herein in its entirety. In addition, systems and methods that utilize a spinning porous membrane are also disclosed in U.S. Provisional Patent Application No. 61/537,856, filed on Sep. 22, 2011, International (PCT) Application No. PCT/US2012/028522, filed Mar. 9, 2012, International (PCT) Application No. PCT/US2012/054859, filed Sep. 12, 2012, and U.S. patent application Ser. No. 14/574,539, filed Dec. 18, 2014, the contents of each are incorporated herein by reference. The references identified above describe a membrane covered spinner having an interior collection system disposed within a stationary shell.

It will be appreciated that a reusable apparatus utilizing a principle of separation other than a spinning membrane, such as centrifugation, but still requiring a disposable fluid circuit may also be used in the methods and systems described herein.

Figure 1:
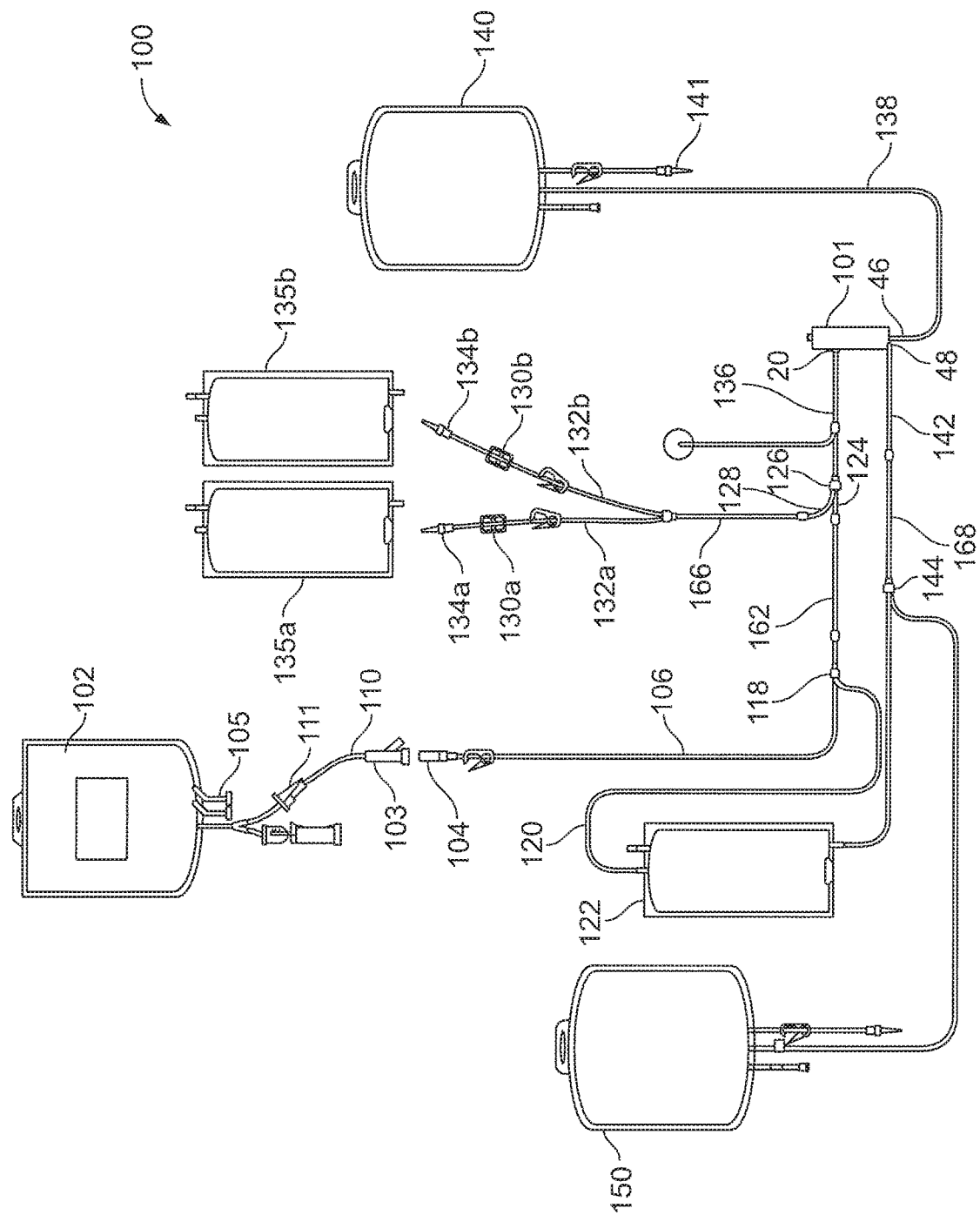
FIG. 1 is a schematic view of one embodiment of a disposable fluid circuit for use in the systems and methods described herein.

Turning first to FIG. 1, the systems described herein preferably include a disposable fluid circuit for use in the processing of the biological fluid (e.g., suspension of biological cells). Fluid circuit 100 is adapted for mounting onto a reusable hardware component, described below. Circuit 100 may include an integrated separation device, such as, but not limited to, the spinning membrane 101 described herein. Circuit 100 may also include filtrate bag or container 140, retentate or final container or bag 150, and in-process container 122. Disposable fluid circuits of the type described below may further include sampling assemblies (not shown) for collecting samples of biological cells or other intermediate products obtained during the biological fluid processing.

As will be seen in the Figures and described in greater detail below, the disposable fluid processing circuit includes tubing that defines flow paths throughout the circuit, as well as access sites for sterile or other connection to containers of processing solutions, such as wash solutions, treating agents, and sources of the biological fluid (e.g., cell suspension). As will be apparent from the disclosure herein, a single source container 102 or multiple source containers (102a, 102b, 102c, as shown in FIG. 2) for processing may be attached in sterile fashion to circuit 100.

Figure 2:
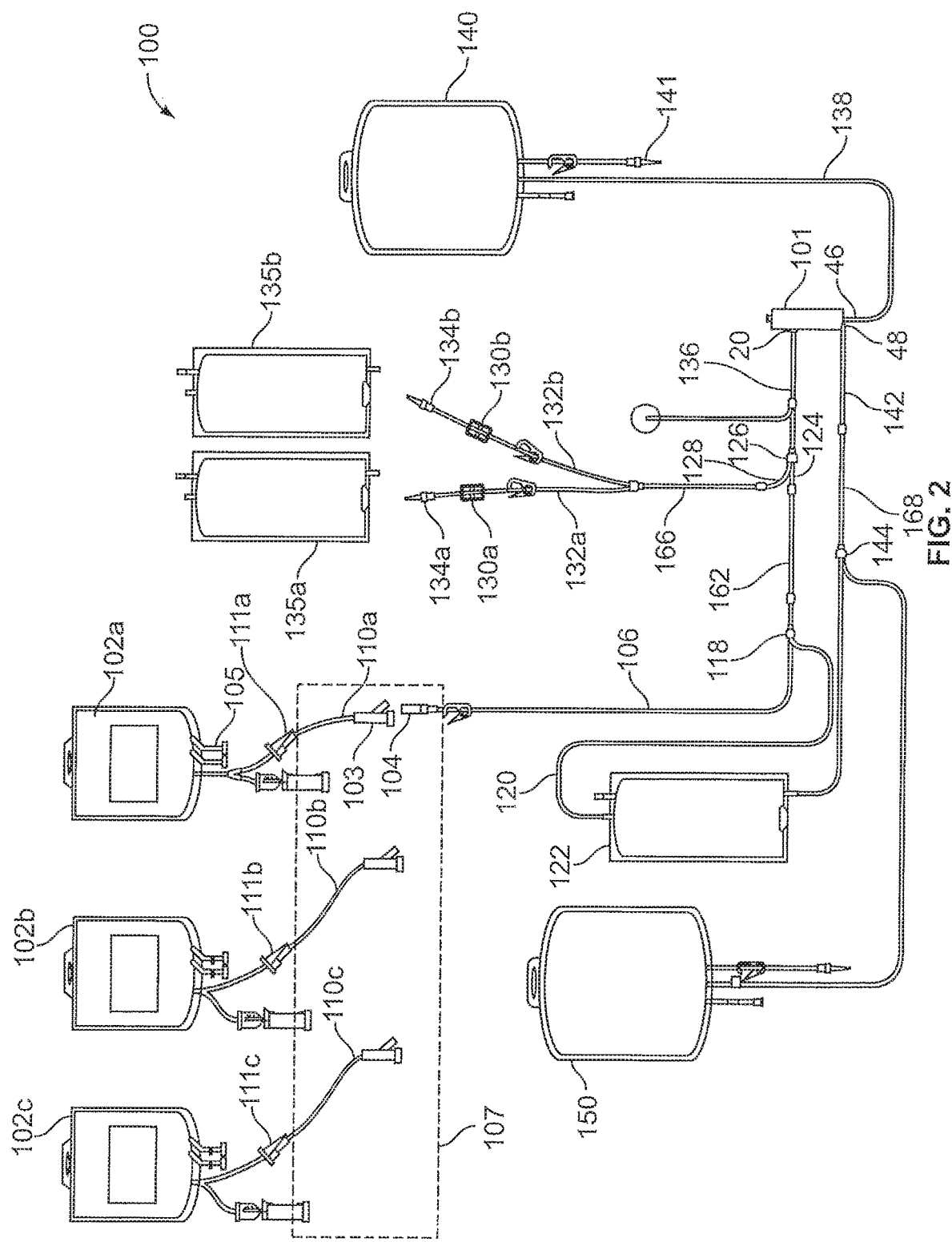
FIG. 2 is a schematic view of another embodiment of disposable fluid circuit with multiple source containers for use in the systems and methods described herein.

As shown in FIGS. 1 and 2, the tubing of circuit 100 includes spaced tubing segments identified by reference numerals 162, 166, 168. The tubing segments are provided for mating engagement with the peristaltic pumps of the reusable hardware apparatus 200, also discussed below and shown, for example, in FIG. 5. The containers and the plastic tubing are made of conventional medical grade plastic that can be sterilized by sterilization techniques commonly used in the medical field, such as, but not limited to, radiation or autoclaving. Plastic materials useful in the manufacture of containers and tubing in the circuits disclosed herein include plasticized polyvinyl chloride. Other useful materials include acrylics. In addition, certain polyolefins may also be used.

The biological fluid, such as a (biological) cell suspension, to be processed is typically provided in a source container 102, shown in FIG. 1 as (initially) not connected to the disposable set. As noted above and shown in FIG. 2 and discussed in greater view below, one or more source container(s) (102a, 102b, 102c) may be connected (in sterile fashion) at the time of use. In one embodiment, wherein cryopreserved biological cells are to be processed, it may be preferable to connect each container of multiple containers just prior processing to maintain the cells at the desired temperature right up to the time of processing. Source container(s) 102 may include one or more access sites 103, 105, one of which may be adapted for (sterile) connection to fluid circuit 100 at docking site 104. Preferably, source containers may be attached in a sterile manner by employing sterile docking devices, such as the BioWelder, available from Sartorius AG, or the SCD IIB Tubing Welder, available from Terumo Medical Corporation. A second access port 105 may also be provided for extracting fluid from the source containers(s) 102. In accordance with the methods and systems described herein and as previously noted, multiple source containers 102a, 102b, 102c, etc., may be provided for the processing of larger volumes of the biological fluid. While three (3) source containers are shown, it will be appreciated that more (or fewer) than three source containers may be processed in the course of a processing procedure. Alternatively, a single, larger volume source container 102 may be attached in lieu of multiple source containers, as shown in FIG. 1. Depending on the type of cells being processed, and the desired concentration of the final cell product, source containers may vary in volume from "standard" containers capable of accommodating a volume of approximately 250-1000 ml to larger-sized source containers that can hold many liters of source fluid such as 5, 10, 50 and up to 100 or more liters.

As shown in FIG. 2, where multiple source containers 102a, 102b, and 102c are to be processed, circuit 100 may optionally include a manifold 107 (shown in dashed lines), or other branched member that receives and communicates with individual source lines 110a, 110b, and 110c. Manifold 107 or other branched member is in fluid communication with primary source line 106, as shown. Flow through source line 110 (FIG. 1), or multiple, individual source lines 110a, 110b, and 110c may be manually controlled by roller, slide clamp or Roberts-type clamps 111 (FIGS. 1) or 111a, 111b, and 111c (FIG. 2).

With further reference to FIGS. 1 and 2, tubing (source line) 106 is connected to downstream branched-connector 118. Branched-connector 118 communicates with tubing 106 and tubing 120, which provides a fluid flow path from "in-process" container 122, described in greater detail below. Tubing segment 124 extends from branched-connector 118 and is joined to a port of further downstream branched-connector 126. A separate flow path defined by tubing 128 is also connected to a port of branched-connector 126.

In accordance with the fluid circuit of FIGS. 1 and 2, one or more container(s) 135a/135b of priming/wash or other processing/treating/buffering solution may be attached to fluid circuit 100. As further shown in FIGS. 1 and 2, tubing 132a, 132b (defining a flow path) preferably includes and terminates in an access site such as spike connector 134a, 134b. Access sites 134a/134b are provided to establish flow communication with containers 135a/135b (shown in FIGS. 1 and 2) of a priming/wash fluid, such as saline or other solution. More preferably, flow communication between tubing 132a, 132b and a container of priming/wash solution may be achieved by sterile connection device, such as, but not limited to, the previously mentioned Terumo SCD IIB. Tubings 132a, 132b may include in-line sterile barrier filters 130a, 130b, for filtering any particulate from a fluid before it enters the flow path. The priming/wash solution flows from the wash fluid source through tubing segment 132a, and then passes through tubing 128 to the input of the branched-connector 126 described above. The priming/wash solution then flows through tubing segment 124 and source line 106 to one or more source containers (See FIGS. 1 and 2). It should be noted that access site 134b may be used to establish fluid communication with additional containers of priming/wash solution (as shown) or other solutions and/or agents.

As further shown in FIGS. 1 and 2, tubing segment 136 defines a flow path connected at one end to branched-connector 126 and to an inlet port 20 of the separator 101. Preferably, in accordance with the present disclosure, separation device 101 is a spinning membrane separator of the type previously identified and also described in U.S. Pat. No. 5,194,145 and U.S. Pat. No. 5,053,121, which are incorporated herein by reference, U.S. Provisional Patent Application Ser. No. 61/451,903, and PCT/US2012/028522, also previously incorporated herein by reference. In an alternative embodiment, separator 101 may utilize a different separation principle. For example, separator 101 may be a centrifuge.

Figure 3:
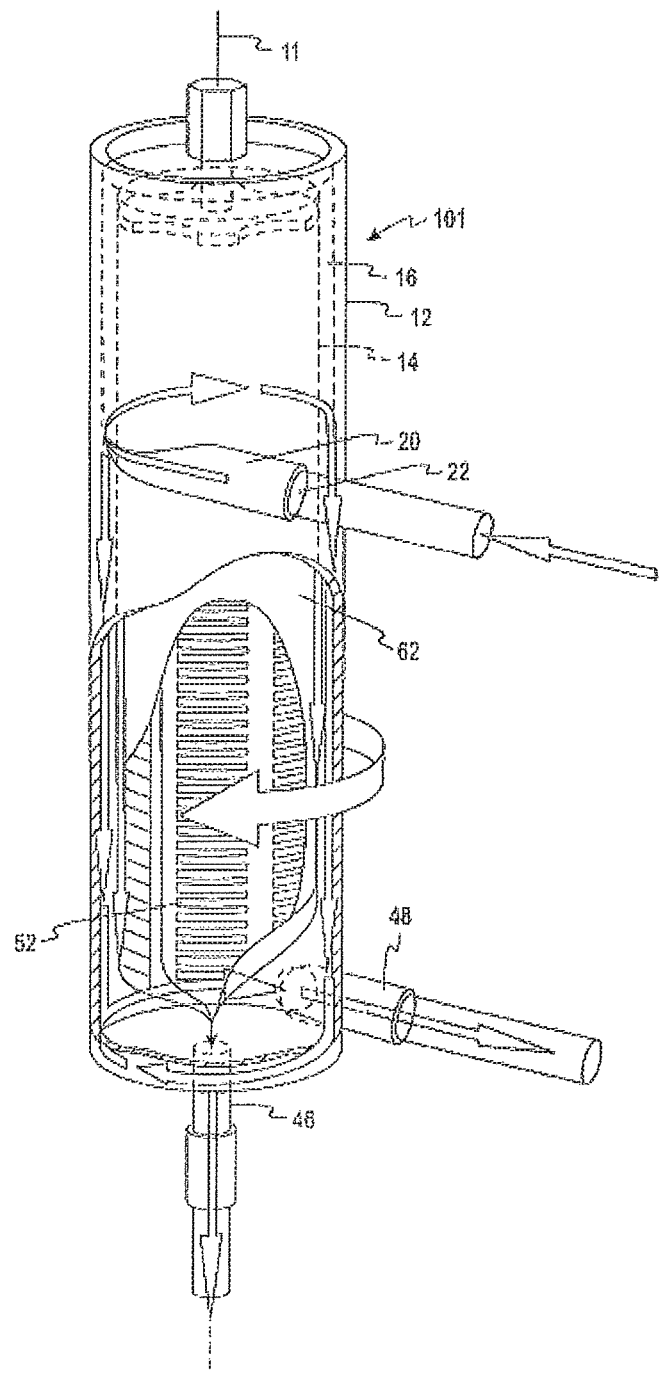
FIG. 3 is a perspective view of the separation device, with a portion of the housing wall broken away.

As seen in FIGS. 1-3, spinning membrane separation device 101 has at least two outlet ports. Outlet 46 of separator 101 receives the separated filtrate and is connected to tubing 138, which defines a flow path to filtrate/cell container 140. The filtrate/cell container may further include connection port 141 for sampling the contents within the filtrate/cell container 140.

Separation device 101 preferably includes a second outlet 48 that is connected to tubing segment 142 for directing the retentate to branched-connector 144, which branches into and defines a flow path to one or more in-process containers 122 and/or a flow path to a "final" retentate container 150.

Turning to FIG. 3, spinning membrane separation device 101 is shown in greater detail. Such a device 101 forms part of the disposable circuit 100.

Device 101 includes a generally cylindrical housing 12, mounted concentrically about a longitudinal vertical central axis. An internal member 14 is mounted concentric with the central axis 11. Housing 12 and internal member 14 are relatively rotatable. In the preferred embodiment, as illustrated, housing 12 is stationary and internal member 14 is a rotating spinner that is rotatable concentrically within cylindrical housing 12, as shown by the thick arrow in FIG. 5. The boundaries of the flow path are generally defined by gap 16 between the interior surface of housing 12 and the exterior surface of rotary spinner 14. The spacing between the housing and the spinner is sometimes referred to as the shear gap. The shear gap may be approximately 0.02-0.06 inches (0.05-0.15 cm) and may be of a uniform dimension along axis 11, for example, where the axis of the spinner and housing are coincident. The shear gap may also vary circumferentially for example, where the axis of the housing and spinner are offset.

The shear gap also may vary along the axial direction, for example preferably an increasing gap width in the direction. Such a gap width may range from about 0.02 to about 0.075 inches (0.05-0.19 cm). The gap width could be varied by varying the outer diameter of the rotor 52 and/or the inner diameter of the facing housing surface. The gap width could change linearly or stepwise or in some other manner as may be desired. In any event, the width dimension of the gap is preferably selected so that at the desired relative rotational speed, Taylor-Couette flow, such as Taylor vortices, are created in the gap.

Biological fluid is fed from an inlet conduit 20 through an inlet orifice 22, which directs the fluid into the fluid flow entrance region in a path tangential to the circumference about the upper end of the spinner 14. At the bottom end of the cylindrical housing 12, the housing inner wall includes an exit orifice 48. Cylindrical housing 12 is completed by a bottom end housing terminating in an outlet orifice 46 concentric with the central axis.

In the illustrated embodiment, the surface of the rotary spinner 14 is at least partially, and is preferably substantially or entirely, covered by a cylindrical porous membrane 62. The membrane 62 may have a nominal pore size between 0.8 and 10 microns (μm), for example. Membranes may be fibrous mesh membranes, cast membranes, track-etched membranes or other types of membranes that will be known to those of skill in the art. For example, in one embodiment, the membrane may have a polyester mesh (substrate) with nylon particles solidified thereon, thereby creating a tortuous path through which only certain sized components will pass. In an embodiment, the nylon membrane may have a pore size of approximately 0.8 μm and a thickness of approximately 150 μm or greater. Membranes of this type will typically retain all cellular components (e.g., red blood cells, white blood cells) and certain formed blood components, e.g., platelets. In another embodiment, the membrane may be made of a thin (approximately 10 μm thick) sheet of unsupported polycarbonate, for example, with a pore size of approximately 4.0 μm. In this embodiment, pores (holes) may be cylindrical and larger than those described above. The pores may be sized to allow small formed components (e.g., platelets, microparticles, etc.) to pass, while the desired cells (e.g., white blood cells and larger red blood cells) are collected.

FIG. 4 shows the front panel 201 of reusable hardware processing apparatus 200. Apparatus 200 may be of compact size suitable for placement on a table top of a lab bench and adapted for easy transport. Alternatively, apparatus 200 may be supported by a pedestal that can be wheeled to its desired location. In any event, as shown in FIG. 3, apparatus 200 includes a plurality of peristaltic pumps, such as pumps 202, 204, and 206 on front panel 201. Pump segments 166, 162, and 168 of the disposable fluid circuit (described above) are selectively associated with peristaltic pumps 202, 204, and 206. The peristaltic pumps articulate with the fluid sets of FIGS. 1 and 2 at the pump segments identified by reference numerals 162, 166, 168 and advance the priming solution and ultimately the cell suspension or other fluid within the disposable set, as will be understood by those of skill in the art. Apparatus 200 also includes clamps 210, 212, 214, 216, and 218. Clamps 210, 212, 214, 216, and 218 are used to control the flow of the cell suspension through different segments of the disposable set.

Apparatus 200 also includes several sensors to measure various conditions. The output of the sensors is utilized by device 200 to operate one or more processing or wash cycles. One or more pressure transducer sensor(s) 226 may be provided on apparatus 200 and may be associated with a disposable set 100 at certain points to monitor the pressure during a procedure. Pressure transducer 226 may be integrated into an in-line pressure monitoring site (at, for example, tubing segment 136), to monitor pressure inside separator 101. Air detector sensor 238 may also be associated with the disposable set 100, as necessary. Air detector 238 is optional and may be provided to detect the location of fluid/air interfaces. In accordance with the system priming described herein, air detector 238 may be used to generate an alert/alarm which may indicate incomplete priming or insufficient processing, requiring some correction and/or intervention by the operator. This is discussed in further detail below.

Apparatus 200 includes weight scales 240, 242, 244, 246, 250, and 252 from which the cell container, in-process container, source container, and any additional container(s) (e.g., wash or priming solution container, retentate container, filtrate container, source container) may depend and be weighed. (While apparatus 200 may include multiple weight scales that can accommodate more than one container of a type of fluid (e.g., source, wash, priming etc.), a single weight scale may be used for multiple, sequentially hung source containers as will be described below). The weights of the containers are monitored by weight sensors and recorded during a washing or other procedure, including during the priming steps described herein. Where multiple source containers are to be processed, some of the source containers may be suspended from a standard I.V. pole or the like (in which case scale measurements would not be taken but pump strokes counted). Similarly, an oversized single container may also be suspended from a separate pole (without a weigh scale that communicates with the system's controller). From measurements of the weight sensors or other parameters, the device, under the direction of the controller, determines whether each container is empty, partially full or full, and controls the components of apparatus 200, such as the peristaltic pumps and clamps 210, 212, 214, 216, 218, 220, and 222. In accordance with the present disclosure, weight sensors may provide volumes of biological fluid in source containers 102 (102a, 102b, 102c, etc.) and monitor the changing volume of priming/wash solutions in containers 135 (a and/or b) during priming, discussed in greater detail below.

Apparatus 200 includes at least one drive unit or "spinner" 248 (FIG. 3), which causes the indirect driving of the spinning membrane separator 101. Spinner 248 may consist of a drive motor connected and operated by apparatus 200, coupled to turn an annular magnetic drive member including at least a pair of permanent magnets. As the annular drive member is rotated, magnetic attraction between corresponding magnets within the housing of the spinning membrane separator cause the spinner within the housing of the spinning membrane separator to rotate.

Figure 6:
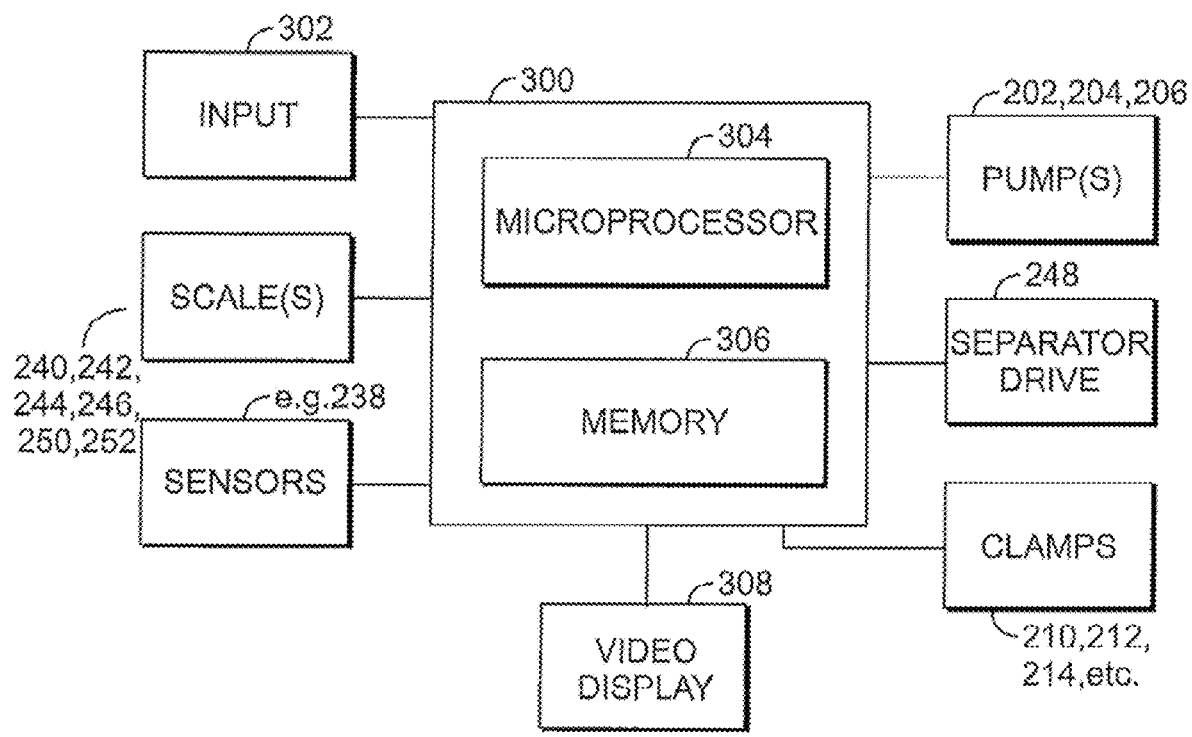
FIG. 6 is a schematic view of the control circuitry, including the controller, of the device of FIGS. 3 and 4.

FIG. 6 is a schematic view of the control unit or "controller" 300 included in device 200 of the present disclosure. The controller 300 may include a microprocessor 304 (which may include multiple physical and/or virtual processors). According to other embodiments, the controller 300 may include one or more electrical circuits designed to carry out the actions described herein. In an embodiment, controller 300 may include a microprocessor and other circuits or circuitry. In addition, the controller 300 may include one or more memories 306. The instructions by which the microprocessor 304 is programmed may be stored on the memory 306 associated with the microprocessor 304, which memory/memories 306 may include one or more tangible non-transitory computer readable memories, having computer executable instructions stored thereon, which when executed by the microprocessor 304 may cause the microprocessors 304 to carry out one or more actions as described herein.

As is also illustrated in FIG. 6, controller 300 may be coupled to one or more of the structures described above, for example, to receive information (e.g., in the form of signals) from these structures or to provide commands (e.g., in the form of signals) to these structures to control the operation of the structures. As illustrated in FIG. 6, the controller 300 may be coupled to the scales 240, 242, 244, 246, 250, 252, etc., (seen in FIG. 3) that hold solution containers or that are provided to collect blood components, the sensors associated with device 200, clamps 210, 212, 214, 216, 218, 220, 222, and the at least one input 302 to receive information from those devices. Additionally, the controller 300 may be coupled to pumps 202, 204, and 206 and the separator drive unit 248 to provide commands to those devices and to control their operation. It may also be possible that the controller 300 receives information from and provides commands to a given structure, such as one of the structures already mentioned. The controller 300 may be directly electrically connected to these structures to be coupled to them, or the controller 300 may be directly connected to other intermediate equipment that is directly connected to these structures to be coupled to them.

The at least one input 302 may include a number of different devices according to the embodiments described herein. For example, the input 302 could include a keyboard or keypad by which a user may provide information and/or instructions to the controller 300. Alternatively, the input 302 may be a touch screen, such as may be used in conjunction with a video display 308 that is disposed on the front panel of the device 10, the video display 308 also being coupled to the controller 300. The assembly of the input/touch screen 302 and video display 308 may be one of the afore-mentioned structures to which the controller 300 is coupled from which the controller 300 receives information and to which the controller 300 provides commands. According to still other embodiments, the input 302 may be in the form of computer equipment that permits the cell processing system including the controller 300 to communicate (whether via wires, cables, etc. or wirelessly) with other cell processing systems over a local network, or with other cell processing systems or other computer equipment (e.g., a server) over local networks, wide area networks, or the Internet. According to such an embodiment, the input may include an internal transmitter/receiver device.

The methods of processing large volumes of biological cell suspensions will now be described.

Figure 7:
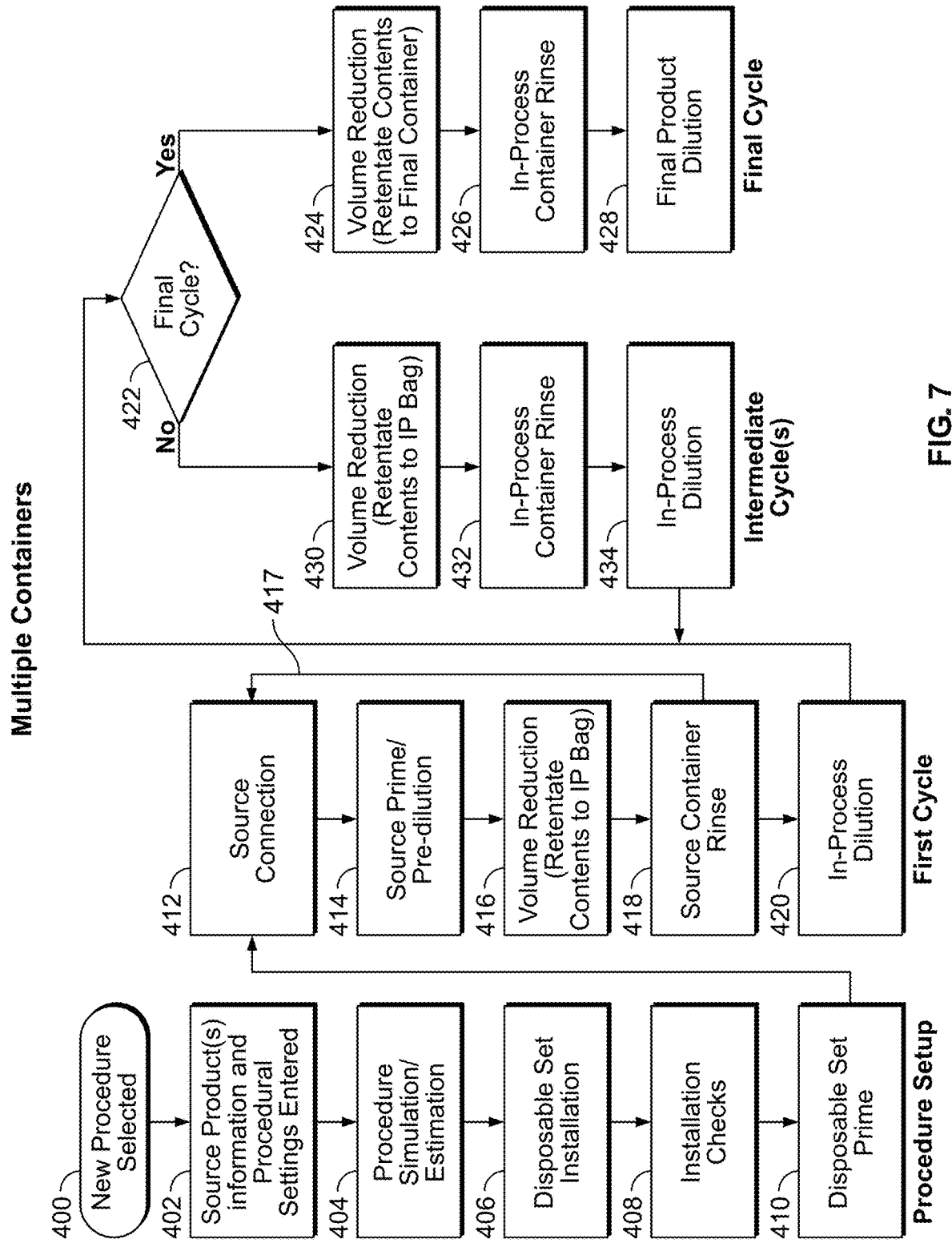
FIG. 7 is a flow chart setting forth steps of the method of sequential processing of multiple containers of a biological cell suspension in accordance with the systems shown and described herein.

As discussed, above, cell suspension processing in accordance with methods and systems described herein can be from multiple or single, large volume container. FIG. 7 sets forth steps in processing of a biological cell suspension from multiple containers. Typically, the suspensions contained within multiple source containers are intended to be concentrated (volume-reduced) to arrive at a final concentrated cell product. Such final cell product may be used in a therapeutic treatment of a patient by direct infusion or after being subjected to further processing such as cell culturing, phenotypic cell selection, cryopreservation, as well as other post collection processes as defined by the end user.

As shown in FIG. 7, processing may commence with the selection of the particular procedure (block 400). At the outset of the selected procedure, the operator may enter certain product and processing parameters, as shown at block 402. For example, the operator may enter the concentration of the cells in the multiple source containers and/or the desired concentration of the final cell product. Original cell concentrations may be determined by prior sampling of the cell suspension or by other parameters (e.g., pH, glucose, lactate) that may be indicative of a cell concentration. Alternatively, the cell concentration may be a pre-set, default value typical for the particular cell suspension to be processed. Additional parameters that may be entered by the operator may include the volume of the suspension in each of the multiple containers. The volumes of cell suspension contained in the multiple source containers may be provided in advance of the procedure or can be automatically determined by the system controller based on the weight of the container(s) as measured by the weight scales (244, 246). Where multiple containers of cell suspensions are to be processed, the number of containers may also be entered. Still other parameters that may be selected or entered by the operator is a final concentration and/or volume for the fully processed cell suspension contained in the multiple source containers.

The controller 300 may receive the processing parameters via the input 302. As mentioned above, the controller 300 may receive the process parameters by operator from the memory 306 associated with the controller 300, some or all of which may be modified by the operator via the input 302, for example.

Based on the parameters provided and entered, the system will calculate the processing conditions such as flow rate, pump speeds, volumes of consumed diluent (wash media), volumes of generated filtrate (waste), processing times, washout percentage or fold dilution (e.g., the percentage of original supernatant that has been removed to the filtrate stream) and process residuals for processing the entire volume of the cell suspension provided in the multiple containers. As described in U.S. patent application Ser. No. 15/456,853, the contents of which is incorporated herein by reference, the system, under the direction of the controller, will preferably conduct a preliminary process evaluation i.e., procedure simulation/estimation (block 404) to determine, among other things, whether the processing conditions for the volume/concentration of the cell suspension are acceptable and/or fall within acceptable or pre-set ranges. For example, in large volume processing, the system may initially predict a higher than desired inlet flow rate in order to arrive at the desired final concentration (which could result in potentially exposing the cells to excessive shear in the tubing). In any event, should the procedure settings result in incompatible conditions, (including, but not limited to a final concentration that cannot be achieved, filtrate production that exceeds the available bag volume), the operator may be alerted to adjust certain parameters and/or add additional collection containers.

Other actions may be automatically initiated by the controller during the procedure/simulation estimation step (block 404). For example, if the concentration of cells in one or more source containers exceeds a (pre-set) maximum filter concentration, the system under the direction of the controller will automatically dilute (at block 414) the "feed" as it flows toward separator 101.

Once the procedure/simulation estimation step (block 404) is completed, the operator installs disposable fluid processing circuit 100 onto reusable hardware unit 200 (block 406). The system may then undergo a series of installation checks (block 408). Once these checks are completed, disposable fluid circuit 100 is ready for priming (block 410). Priming of the fluid circuit may generally proceed as described in Ser. No. 15/600,447, the contents of which are incorporated herein by reference.

After priming of the fluid circuit, multiple source containers may be connected to the circuit in sterile fashion, as previously described (block 412) and as shown on FIG. 5. While FIG. 5 shows multiple source containers (102(*a*)-(*c*)) attached, it is not necessary to attach all source containers simultaneously. More preferably and as shown in FIG. 7 by loop 417, source containers 102 may be attached to the fluid circuit sequentially, one after another in the course of processing (i.e., as processing of one source container is completed, the next container is attached to the circuit etc. until all source containers have been processed). It will be understood that while the source containers 102 may be attached to circuit 100 one at a time during processing, parameters for source container volume and source concentration for all of the multiple containers 102 to be processed will have been entered or selected at the outset of the procedure e.g., block 402 or otherwise pre-set as an estimated (and typically the same) default value. This allows processing to continue without the need for the operator to enter source container parameters at the time each container (of multiple source containers) is attached (block 412).

Once source container 102 has been attached, the system may (optionally) commence the source prime/pre-dilution step (block 414) described above i.e., in the event that the concentration of cells in one or more source containers exceeds a (pre-set) maximum filter concentration, the controller will automatically effect dilution (at block 414) of the "feed" as it flows toward separator 101.

Processing of the cell suspension from source container 102 proceeds by introducing the cell feed into separator 101 through inlet port 20 and into gap 16 of the separator where under the influence of the spinning membrane, the cell suspension is separated into concentrated cells (retentate) which exit through one of the outlets to in-process container 122 (block 416), and filtrate which passes through the pores of the spinning membrane and exits through a different outlet to waste/filtrate container 140.

As the source container parameters such as, but not limited to, source volume are entered or selected (by default) at the outset of processing (block 402), the system will recognize when the entire or substantially the entire contents of the source container has been processed. Alternatively, the system controller may receive information by weigh scales 244, 246 or air detector 238. The controller may then effect the source container rinsing step of block 418 wherein source container 102*a* may be rinsed with a rinsing solution (such as saline from container 135) and collected in the in-process container 122. Also, once the entered source volume has been processed, as determined by the controller from parameters entered at block 402 and/or based on reading from weigh scales 244,246 conveyed to controller 300, the operator may attach the next source container 102*b*, if not previously attached. The controller may be configured to pause processing for a selected period of time to allow the operator to attach the next in-sequence container without additional data entry. As shown by loop 417 in FIG. 7, sequential processing (steps in blocks 414, 416, 418) of multiple source containers are repeated for each container until the entire volume of the cell suspension in all of the source containers 102 has been processed, with the retentate being collected in in-process container 122.

Depending on the desired targeted concentration for the final product entered at the outset of the procedure (block 402), the retentate residing in in-process container 122 (which is the combined cell output of the multiple source containers) may be further processed in a final cycle or in one or more intermediate cycles before undergoing the final cycle, as shown in FIG. 7. Retentate residing in in-process container 122 may be diluted (block 420) to below a maximum filter concentration or a target dilution volume predetermined by the operator and subjected to a final cycle (block 422) wherein the retentate is introduced for a final time into separator 101 where it is concentrated (volume-reduced) and expressed to one or more final container(s) 150 (block 424). In-process container 122 may be rinsed (block 426) during the final cycle, with the rinse being introduced into final container 150. An additional dilution of the final product may also be performed to arrive at a final concentration (block 428).

Alternatively, if after sequential processing of multiple source containers, further concentration or volume reduction may be needed or desired to arrive at the targeted final concentration, the retentate in in-process container 122 may, after dilution (block 420) be subjected to one or more intermediate cycles as depicted in blocks 430, 432 and 434 prior to the final cycle described above. During such intermediate cycling, diluted retentate is introduced into separator 101, processed and the newly concentrated retentate is returned to in-process container 122 where it is diluted (block 434) for another intermediate cycle or for the final cycle (422).

Thus, in accordance with the present disclosure, multiple source containers can be processed sequentially using a single fluid circuit to arrive at a final concentration for the final product.

In another embodiment, as shown in FIG. 1, processing may proceed from a single, typically large(r)-volume, source container rather than the multiple containers. Such containers may contain a cell suspension volume of approximately 1-100 liters. Where the source containers are too large to suspend from hardware unit 200, a separate pole (not shown) with a hook for receiving such container may be provided.

In accordance with the systems and methods described herein, processing from a single container of a large volume of a cell suspension will preferably proceed in "batch" fashion. By "batch" processing, it is meant that rather than continuously processing the entire contents of a source container, pre-determined volumes or "batches" of source fluid are withdrawn from the single source container and fully processed. Once the first pre-determined volume has been processed, the system will automatically withdraw and process a second pre-determined volume or "batch" of source fluid from the single source container. This process will be repeated until all of the source fluid has been processed. The steps in such "batch" processing are shown in FIG. 8.

Figure 8:
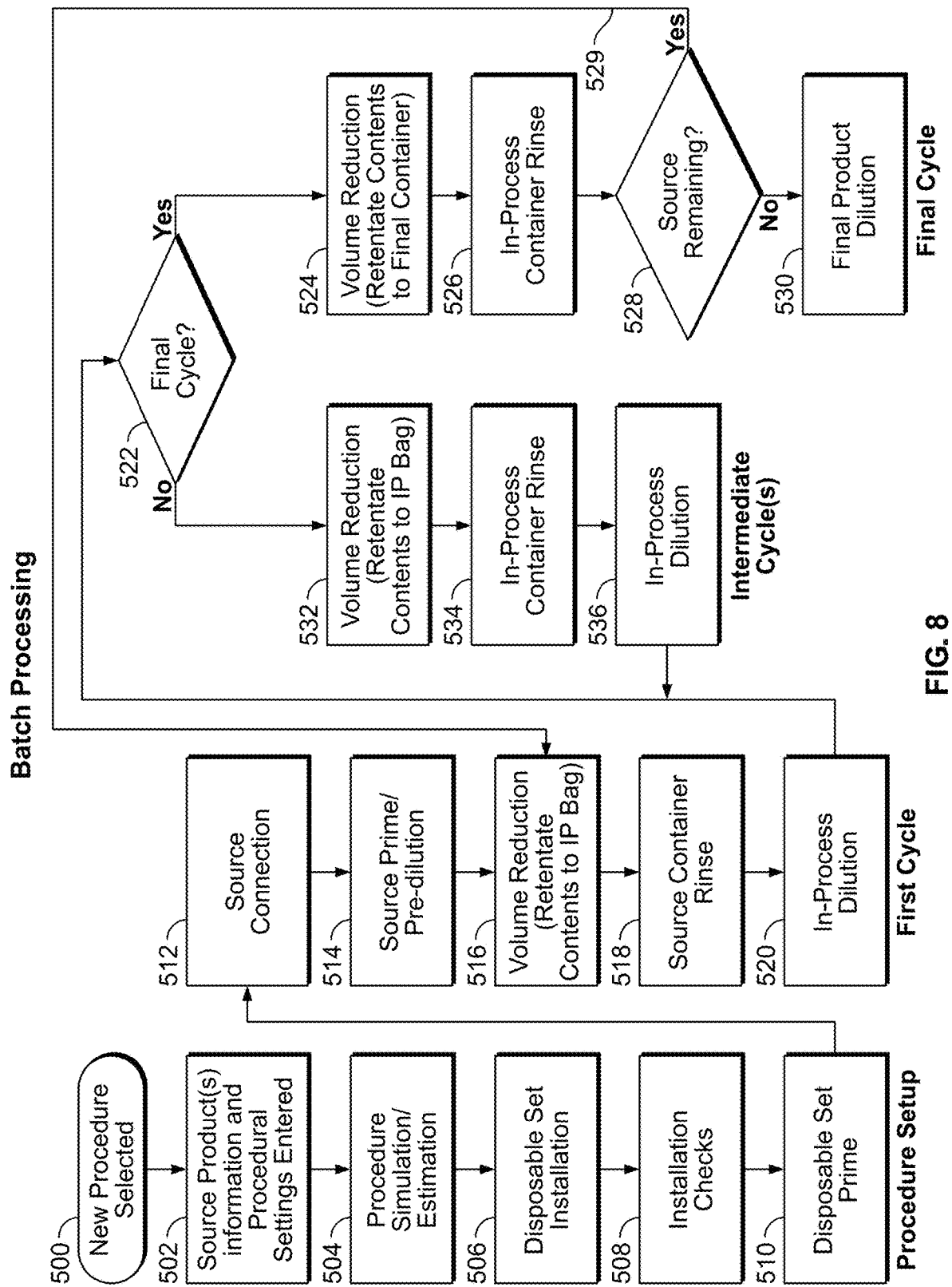
FIG. 8 is a flow chart setting forth steps of the method of batch processing of a single, large volume container of a biological cell suspension in accordance with the systems shown and described herein.

As seen in FIG. 8, it will be appreciated that many of the steps in batch processing will be similar and often identical to the steps described above in connection with multiple container, sequential processing (FIG. 7). For example, as shown in block 500 of FIG. 8, the operator selects the procedure and then enters the desired source product information and procedural settings (block 502). As also described above, source product information may include the cell concentration in source container 102, the total volume of the cell suspension in the source container and the number of containers which, in the case, of batch processing is the default number of one (1). Additional procedural settings and information that may be entered include a final target concentration for the concentrated cells. As discussed above, source concentrations may be determined from pre-processing sampling or from pre-set or default values stored in the memory 306 of controller 300, subject to modification by the operator.

Once the applicable parameters have been entered, the system will calculate the processing conditions such as flow rate, pump speeds, volumes of consumed diluent (wash media), volumes of generated filtrate (waste), processing times, washout percentage and other process residuals to effect processing of the multiple batches of source fluid. The system, under the direction of the controller will also automatically undergo a procedure/simulation estimation (block 504) as substantially described above. During the procedure simulation/estimation step 504, the system will determine whether the processing conditions for the volume/concentration of the cell suspension are acceptable and/or fall within the entered or pre-set ranges, as has been generally described above in connection with the sequential processing protocol. For example, if the input configuration results in an output configuration that exceeds the volume of the pre-attached collection containers, the system may prompt the user to attach additional containers for increased capacity.

Once the procedure/simulation estimation step (block 504) is completed, the operator installs disposable fluid processing circuit 100 onto reusable hardware unit 200 (block 506). The system will undergo a series of installation checks (block 508). Once these checks are completed, disposable fluid circuit is ready for priming (block 510). Priming of the fluid circuit may generally proceed as described in Ser. No. 15/600,447, the contents of which are incorporated herein by reference. After priming of the fluid circuit, single source container 102 may be connected (block 512) to the circuit in sterile fashion, as previously described.

Further processing continues as shown in blocks 514, 516 and 518 and is generally analogous to steps 414, 416 and 418 described in connection with the sequential processing shown in FIG. 7. Unlike sequential processing, however, there is no loop 417 in batch processing wherein additional source containers are connected upon emptying of the container. In batch processing as shown on FIG. 8, after the final batch has been processed, source container 102 may be rinsed (block 518) and the concentrated cell in the in-process container 122 is diluted, the system under the direction of the controller will determine whether to proceed to final cycle 522 or, if further volume-reduction is required to arrive at the targeted final concentration, proceed to one or more intermediate cycles (steps 532, 534 and 536). If the separated and concentrated cells in in-process container 122 are ready for the final cycle 522, the concentrated cells (retentate) undergoes a final volume reduction in separator 101 and the retentate of this step is expressed to final container 150.

During the final cycle, after in-process container is rinsed (with wash solution in container 135), the system, upon determining that there is additional source fluid remaining in source container 102, will initiate (step 529) another draw of a batch of source fluid and repeat the volume reduction and other processing steps shown in blocks 516, 518, 520 as well as the steps of the intermediate cycle(s) 532, 534 and 536 and final cycle (524, 526, 528 and 530). Step 528 will prompt additional batch draws until the volume of source fluid is exhausted.

OTHER EXAMPLES

Aspects of the present subject matter described above may be beneficial alone or in combination with one or more other Aspects, as described below. Without limiting the foregoing description, in accordance with a first Aspect (i.e., Aspect 1) of the subject matter, there is provided a system for processing biological cell suspensions. The system includes a disposable fluid circuit that includes a separation device, a fluid flow path in flow communication with said separation device and one more fluid access devices for establishing fluid communication between the flow path and one or more containers of a biological cell suspensions. The system also includes a reusable hardware unit with a separation device drive unit for receiving said separation device, an operator input and a controller coupled to said input wherein the controller is configured to receive a processing parameter comprising the total volume of biological cell suspension to be processed from one or more source containers. The controller is also configured to receive a processing parameter comprising the concentration of cells in said one or more source containers. In addition, the controller is configured to calculate the number of draws from one or more source containers and/or the volume of each of said draws.

Aspect 2. The system of Aspect 1 wherein the controller is further configured to receive a processing parameter comprising a final targeted cell concentration and to calculate the number and volume of draws based at least in part on said targeted cell concentration.

Aspect 3. The system of any one of Aspects 1 and 2 wherein the controller is configured to receive a processing parameter comprising the volume of the biological cell suspension to be processed and the number of biological cell suspension source containers.

Aspect 4. The system of any one of Aspects 1 through 3 wherein the controller is configured to receive a processing parameter comprising the number of a plurality of biological cell source containers, the actual or estimated volume of each of the plurality of source containers and/or the concentration of biological cells in each of the plurality of source containers.

Aspect 5. The system of Aspect 4 wherein the volume and/or concentration of each of the plurality of biological cell source containers are estimated to be the same.

Aspect 6. The system of any one of Aspects 1 through 5 wherein the controller is configured to sequentially draw a series of predetermined amounts of a biological cell suspension from a single source container of the biological cell suspension.

Aspect 7. The system of any one of Aspects 1 through 6 wherein the disposable fluid circuit comprises an in-process container, one or more waste containers and one or more final collection containers.

Aspect 8. The system of any one of Aspects 1 through 7 wherein the controller is configured to generate a prompt when the contents of one of a plurality of source containers have been processed by the system.

Aspect 9. The system of any one of Aspects 1 through 7 wherein the controller is configured to draw a pre-determined volume of a biological cell suspension from a sole source of the suspension.

Aspect 10. The system of any one of Aspects 1 through 9 wherein the separation device comprises a membrane mounted onto a spinning member within a separator housing including an inlet and one or more outlets and a gap defined by the membrane and an inner surface of said housing.

Aspect 11. The system of any one of Aspects 1 through 10 wherein the disposable fluid circuit is adapted for connection to a plurality of source containers.

Aspect 12. An automated method for processing a biological cell suspension from one or more source containers of a biological cell suspension comprising: receiving a processing parameter comprising the total volume of biological cell suspension to be processed from one or more source containers; receiving a processing parameter comprising the concentration of cells in the one or more source containers; calculating the number of draws from said one or more source containers and the volume of each draw; and drawing the biological cell suspension from the one or more source containers.

Aspect 13. The method of Aspect 12 further comprising receiving a target concentration of a processed final cell product.

Aspect 14. The method of any one of Aspects 12 through 13 further comprising generating an alert if the final target concentration of a processed final cell product cannot be achieved with the biological cell suspension to be processed.

Aspect 15. The method of any one Aspects 13 through 14 further comprising calculating the number of draws from the one or more source containers and the volume of each of the draws based upon the final target concentration of a processed final cell product to the total volume of the biological cell suspension to be processed.

Aspect 16. The method of any one of Aspects 12 through 15 comprising drawing a biological cell suspension from one or more source containers of biological cell suspension into a disposable fluid circuit comprising one or more final collection containers, one or more waste containers and an in-process container.

Aspect 17. The method of any one of Aspects 12 through 15 comprising comparing the final target concentration of a processed final cell product to the total volume capacity of one or more collection containers.

Aspect 18. The method of any one of Aspects 16 through 17 comprising concentrating the biological cells and holding the concentrated biological cells in the process container.

Aspect 19. The method of Aspect 18 further comprising drawing a pre-determined volume of the biological cell suspension from the one or more source containers during the holding.

Aspect 20. The method of Aspect 19 further comprising continuously adding concentrated biological cells to the in-process container.

Aspect 21. The method of any one of Aspects 18-20 comprising monitoring the concentration of the concentrated biological cells in the in-process container.

Aspect 22. The method of any one of Aspects 12-21 comprising processing between 1-100 liters of a biological cell suspension using a single fluid circuit.

Aspect 23. The method of Aspect 22 comprising processing the biological cell suspension from a single container.

The description provided above is intended for illustrative purposes only and is not intended to limit the scope of the invention to any specific method, system, or apparatus, or device described herein except as may be explicitly delineated above.

The invention claimed is:

1. A system for processing large volumes of biological cell suspensions from a plurality of containers of a biological cell suspension to arrive at a therapeutically useful concentration comprising:
   a) a disposable fluid circuit including a separation device, a fluid flow path in flow communication with said separation device and one or more fluid access devices for establishing fluid communication between said flow path and a plurality of source containers of a biological cell suspension and one or more containers of one or more processing solutions, an in-process container for collecting concentrated cells during multiple processing cycles and a final collection container wherein said in-process container is in openable fluid communication with said separation device, said source container and said final container;
   b) a reusable hardware unit comprising a separation device drive unit for receiving said separation device and for receiving said disposable fluid circuit by mounting said circuit on said hardware unit, an operator input and a controller for directing the processing of the biological cell suspension coupled to said input, the controller configured:
      i. to receive a processing parameter comprising the total number of the plurality of source containers of the biological cell suspension;
      ii. to receive a processing parameter comprising the total volume of the biological cell suspension to be processed from the plurality of source containers;
      iii. to receive a processing parameter comprising the concentration of cells in said plurality of source containers;
      iv. to calculate the number of draws from said plurality of source containers and the volume of each said draw based on one or more of said processing parameters;
      v. to direct the withdrawal of said biological cell suspension from said plurality of source containers in accordance with said calculated number of draws;
      vi. to determine if the concentration of cells in each of said plurality of source containers exceeds a pre-set maximum filter concentration;
      vii. to effect the dilution of said cells in each of said plurality of containers where the controller determines that the concentration of cells exceeds the pre-set maximum filter concentration such that said concentration of cells does not exceed the pre-set maximum filter concentration; and
      viii. to direct the flow of at least one of said processing solutions to rinse each of said plurality of source containers and said in-process container after withdrawal of said biological cell suspension within one of said plurality of source containers is completed.

2. The system of claim 1 wherein said controller is further configured to receive a processing parameter comprising a final targeted cell concentration and wherein said controller is configured to calculate the number and volume of draws based at least in part on said targeted cell concentration.

3. The system of claim 1 wherein said controller is configured to receive an additional processing parameter comprising the volume of said biological cell suspension to be processed and the number of biological cell suspension source containers, with the controller calculating the number of draws from said plurality of source containers and the volume of each said draw based on one or more of said processing parameters and said additional processing parameter.

4. The system of claim 1 wherein the controller is configured to receive the volume and/or concentration of each of said plurality of biological cell source containers and to compare the volume and/or concentration of each of said plurality of biological cell source containers to determine whether said volumes and/or concentrations of said plurality of biological cell source containers are the same.

5. The system of claim 1 wherein said disposable fluid circuit comprises one or more waste containers.

6. The system of claim 1 wherein said controller is configured to generate a prompt when the contents of the plurality of source containers have been processed by said system.

7. The system of claim 1 wherein said controller is configured to draw a pre-determined volume of the biological cell suspension from a sole source of said suspension.

8. The system of claim 1 wherein said separation device comprises a membrane mounted onto a spinning member within a separator housing including an inlet and one or more outlets and a gap defined by the membrane and an inner surface of said housing.

9. The system of claim 1 wherein the one or more fluid access devices is a plurality of fluid access devices so that said disposable fluid circuit is adapted for connection to the plurality of source containers simultaneously.

10. An automated method for processing a volume of a biological cell suspension from a plurality of source containers of the biological cell suspension in an automated cell processor including a cell processing apparatus, a fluid circuit mounted on said device and a controller, to arrive at a therapeutically useful concentration of targeted cells said method comprising:
   a) receiving in said controller a processing parameter comprising the total number of source containers of the biological cell suspension;
   b) receiving in said controller a processing parameter comprising the total volume of the biological cell suspension to be processed from the plurality of source containers;
   c) receiving in said controller a processing parameter comprising the concentration of cells in said plurality of source containers;
   d) calculating the number of draws from said plurality of-source containers and the volume of each said draw based on one or more of said processing parameters;
   e) automatically drawing under the direction of the controller said biological cell suspension from said plurality of source containers and processing said biological cell suspension according to the received processing parameters in accordance with said calculated number of draws;
   f) determining if the concentration of cells in any of said plurality of source containers exceeds a pre-set maximum filter concentration;
   g) diluting said cells in any of said plurality of source containers where the concentration of cells exceeds the pre-set maximum filter concentration upon a determination that the concentration of cells exceeds the pre-set maximum filter concentration;

h) collecting processed cells in an in-process container;

i) rinsing each of said plurality of source containers with a rinsing solution after withdrawal of said biological cell suspension within one of said containers of said plurality of source containers is complete;

j) rinsing said in-process container with said rinsing solution; and k) collecting said processed cells and rinsing solution from said in-process container in one or more final collection containers.

11. The method of claim 10 further comprising the controller receiving a final target concentration of a processed final cell product and generating an alert if the final target concentration of the processed final cell product cannot be achieved with the biological cell suspension to be processed.

12. The method of claim 10 further comprising the controller receiving a final target concentration of a processed final cell product and calculating the number of draws from said plurality of source containers and the volume of each of said draws based upon the final target concentration of the processed final cell product to the total volume of the biological cell suspension to be processed.

13. The method of claim 10 comprising the controller receiving a final target concentration of a processed final cell product, comparing the final target concentration of the processed final cell product to a total volume capacity of said one or more final collection containers and based on the comparison, prompting a user to attach additional collection containers if more capacity than the total volume capacity is needed.

14. The method of claim 10 comprising concentrating said biological cells and holding said concentrated biological cells in said in-process container.

15. The method of claim 14 further comprising drawing a pre-determined volume of said biological cell suspension from said plurality of source containers during said holding.

16. The method of claim 15 further comprising continuously adding concentrated biological cells to said in-process container.

17. The method of claim 14 comprising the controller determining the concentration of said concentrated biological cells in said in-process container and adjusting certain parameters if the concentration of said concentrated biological cells is not within an acceptable range.

18. The method of claim 10 comprising processing between 1-100 liters of the biological cell suspension using a single fluid circuit.

* * * * *